United States Patent [19]

Levius

[11] Patent Number: 4,807,608

[45] Date of Patent: Feb. 28, 1989

[54] MECHANICAL PENILE PROSTHESIS

[75] Inventor: Dezso K. Levius, Minnetonka, Minn.

[73] Assignee: American Medical Systems, Minnetonka, Minn.

[21] Appl. No.: 76,354

[22] Filed: Jul. 22, 1987

[51] Int. Cl.[4] ............................................. A61F 2/26
[52] U.S. Cl. ..................................................... 128/79
[58] Field of Search ......................................... 128/79

[56] References Cited

U.S. PATENT DOCUMENTS

| | | | |
|---|---|---|---|
| 4,151,840 | 5/1979 | Barrington | 128/79 |
| 4,187,839 | 2/1980 | Nuwayser et al. | 128/79 |
| 4,392,562 | 7/1983 | Burton et al. | 128/79 |
| 4,522,198 | 6/1985 | Timm et al. | 128/79 |
| 4,541,420 | 9/1985 | Timm et al. | 128/79 |
| 4,545,081 | 10/1985 | Nestor et al. | 128/79 |
| 4,619,251 | 10/1986 | Helms et al. | 128/79 |
| 4,665,902 | 5/1987 | Goff et al. | 128/79 |
| 4,666,428 | 5/1987 | Mattioli et al. | 128/79 |

Primary Examiner—Gene Mancene
Assistant Examiner—Cary E. Stone
Attorney, Agent, or Firm—Arnold, White & Durkee

[57] ABSTRACT

A mechanical penile prosthesis is disclosed. The prosthesis includes a sleeve that encapsulates a linear assembly of cups, an actuating means and a cable. The linear assembly of cups allows the prosthesis to be bent from an erect position to a flaccid position. The actuating mechanism includes a biasing member, a poppet with first and second shoulders, one or more sliding rings, and a flexible tine. Bending the prosthesis from its erect position to its flaccid position causes the poppet to move toward the distal end of the prosthesis, allowing the tines to lock behind the second shoulder. To return the prosthesis to its erect state the prosthesis is bent further until the sliding ring separates the tines, allowing the biasing member to force the second shoulder past the tines; the tines snapping back into a position on the proximal side of the first shoulder. A second poppet positioned at the distal end of the prosthesis or a second sliding ring that envelopes the first sliding ring may be included to allow the prosthesis to be bent into a super flaccid position, allowing easier surgical implantation of the prosthesis.

12 Claims, 4 Drawing Sheets

MECHANICAL PENILE PROSTHESIS

FIELD OF THE INVENTION

This invention relates to penile prostheses. More particularly, the present invention relates to mechanical penile prostheses which may be implanted in a flaccid penis for enabling the achievement of an erectile state.

BACKGROUND OF THE INVENTION

Several types of penile prostheses have been developed for implantation within the penis to simulate an erectile state. Examples include an elongated malleable rod enclosed within a flexible casing and systems in which an implanted prosthesis may have fluid pumped into the prosthesis to effect an erection and drained from the prosthesis to return the penis to the flaccid state.

The present invention relates to mechanical prostheses in which a mechanical actuating device is used to cause the prosthesis to acquire an erectile state and to enable one to operate the prosthesis to return the penis to a flaccid state.

SUMMARY OF THE INVENTION

In accordance with the present invention as embodied and broadly described below, a penile prosthesis is provided for inducing a penile erection upon manual activation of the prosthesis. The prosthesis includes an outer sleeve made of a biocompatible and flexible material. A linear assembly of disklike cups or beads are enclosed within the sleeve. Each cup or bead has a proximal end and a substantially flat distal end. The proximal end has an opening for accommodating the insertion of the distal end of an adjoining cup. The substantially flat distal end has substantially flat inner and outer surfaces. The substantially flat inner surface of the distal end of each cup is in substantially axial alignment with the substantially flat outer surface of the distal end of each adjoining cup, when the prosthesis is in an erect state.

The prosthesis also includes a cable, having distal and proximal ends, that extends longitudinally within the prosthesis. The cable maintains the prosthesis in a state of tension. The prosthesis also includes a means for adjusting the position of the cable, allowing the cable to be moved from a position in which one end of the cable is near the corresponding end of the prosthesis to a position in which that end of the cable is moved away from the corresponding end of the prosthesis. Movement of the cable away from the corresponding end of the prosthesis causes the prosthesis to move from an erect state position until it is locked into a flaccid state position. Further movement of the cable in this same direction allows the prosthesis to release from the position at which it is locked into the flaccid state and to spring back to the erect state position.

In a preferred embodiment, the cups or beads each enclose a substantially bowl shaped cavity. This cavity is bordered by an open upper surface at the cup's proximal end, a generally circular inner wall, and the substantially flat inner surface at the distal end of the cup. The radius of the generally circular inner wall of the cavity preferably decreases from the radius at the proximal end of the cup to the radius at the substantially flat inner surface. In this embodiment the substantially flat outer surface of the distal end of each cup engages the substantially flat inner surface of the distal end of an adjoining cup, when the prosthesis is in an erect state.

The cup's exterior preferably is defined by a generally circular outer wall having a radius that decreases from the radius at the proximal end of the cup to the radius at the substantially flat outer surface of the distal end of the cup. In this embodiment, the lower section of the outer wall of one cup is enclosed within the generally bowl shaped cavity of the adjoining cup, when the prosthesis is in the erect position.

When in this erect position, the outer wall of each cup preferably does not contact the generally circular inner wall that borders the cavity of an adjoining cup. Because of this and because of the shape and arrangement of the cups in this embodiment, they may be engaged in point contact when the prosthesis is bent. This point contact is between the generally circular inner wall of one cup and the generally circular outer wall of an adjoining cup and between the substantially flat inner and outer surfaces of the distal ends of the adjoining cups. This point contact enables the prosthesis to be bent along a relatively small radius.

In this preferred embodiment, the engagement between the substantially flat inner and outer surfaces of the adjoining cups gives the prosthesis optimal column strength when the cups are pulled together to place the prosthesis into the erect state. The arrangement of the generally circular inner wall of one cup with the generally circular outer wall of an adjoining cup, such that they do not contact each other when the prosthesis is in the erect state, enables point contact during bending that permits the prosthesis to be bent along a relatively small radius. At the same time, this arrangement prevents dislodgement of the cups after the cups have been pulled together.

In another preferred embodiment of the present invention, the means for adjusting the position of the cable is a poppet. The poppet is longitudinally arranged at the distal side of the proximal end of the cable. This embodiment of the prosthesis may include a biasing member for exerting a force against the poppet to maintain the poppet in a fixed position.

The poppet in this preferred embodiment may include a first and second shoulder and the prosthesis may further include a restraining means for restraining the movement of these shoulders. The prosthesis, in this embodiment, may be in its erect state when the restraining means engages the poppet at the proximal side of the first shoulder. The prosthesis may be in its flaccid state when the second shoulder engages the restraining means.

The restraining means in this preferred embodiment may include a flexible tine. Such a tine would be movable from a first position in which it may contact the second shoulder, restraining movement of that shoulder, to a second position in which it may not contact the second shoulder and may not restrain the movement of that shoulder.

The flexible tine in this embodiment of this invention may be engaged to a fixed ring that may be located within the sleeve. This fixed ring may encircle the poppet and may encircle a sliding ring that envelopes the poppet. In this embodiment, the sliding ring is aligned with the shoulders, allowing one to move the cable until the sliding ring moves under the tine and moves the tine to a position in which the tine may not contact the second shoulder. Once the tine has been moved to this position, the biasing member forces the poppet, along with the sliding ring and the second shoulder, to the proximal side of the tine. After the sliding ring and second shoulder have been forced past the tine, the tine returns to its first position, in which it may engage the poppet at the proximal side of the first shoulder. The stacking-up of the cups restrains further movement of the biasing member.

This embodiment may further include a means for placing the prosthesis in a super flaccid state. This super flaccid state is the position of the prosthesis after it has been further bent from its flaccid state position. In a preferred embodiment, this means for enabling this additional bending required to place the prosthesis in a super flaccid state consists of a second poppet located near the distal section of the prosthesis. This poppet may have first and second shoulders and include an orifice in the distal end of the poppet. The orifice allows one inserting the prosthesis into the penis to thread a string or suture through the orifice.

In this embodiment, a flexible tine is engaged to this second poppet. When in the super flaccid state, the tine locks behind the first shoulder. To move the prosthesis from the super flaccid state to the flaccid state, one inserting the prosthesis pulls the suture, that was inserted through the orifice in the poppet, causing the poppet to be moved toward the distal end of the prosthesis. The poppet is pulled until the tine locks behind the second shoulder. After this movement is complete, the prosthesis acquires its flaccid state.

As an alternative means for effecting a super flaccid state one may use a first sliding ring, having proximal and distal sections, the distal section having a diameter that is greater than the diameter of the proximal section, and a second sliding ring, enveloping the proximal section of the first ring. In this embodiment, the second ring enables the prosthesis to be placed in a super flaccid state by allowing the distal section of the first sliding ring to be pulled to the distal side of the tine, allowing the tine to lock onto the proximal section of the first ring.

Continuing to pull the cable towards the distal end of the prosthesis causes the second ring to slide along the proximal section of the first ring until it separates the tine from the position in which the tine had locked onto the proximal section of the first ring. After the second ring causes the tine to separate, the biasing member forces the distal section of the first ring and the second shoulder of the poppet against the second ring and forces all three components past the tine to the proximal side of the tine. The tine then snaps back into a position in which it may lock behind the first shoulder. This corresponds to the position in which the prosthesis is in its erect state. The stacking-up of the cups restrains further expansion of the biasing member.

The present invention provides a prosthesis that may be placed in a super flaccid state and thus provides a prosthesis that is relatively flexible compared to other presently available mechanical prostheses. This increased flexibility allows different operative approaches.

Examples of the more important features of this invention have been summarized rather broadly in order that the detailed description may be better understood, and in order that the contribution to the art may be better appreciated. There are, of course, additional features of the invention that will be described below and which will also form the subject of the appended claims.

DESCRIPTION OF PREFERRED EMBODIMENTS

Figure 1:
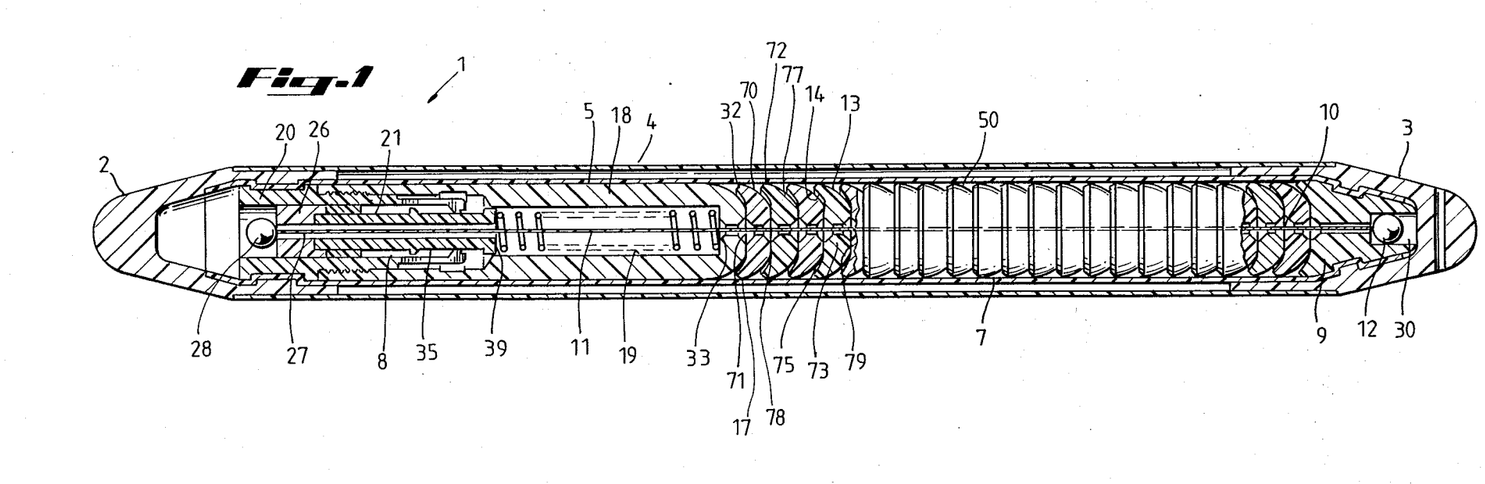
FIG. 1 is a cross-sectional view of an embodiment of the penile prosthesis of the present invention while in the erect state.

FIG. 1 shows a preferred embodiment of the penile prosthesis of the present invention. As shown in FIG. 1, the prosthesis is in its erect state.

FIG. 1 shows a penile prosthesis 1 having a proximal end 2 and a distal end 3. Prosthesis 1 includes a sleeve 4, that preferably includes inner sleeve 5 and outer sleeve 6. Inner and outer sleeves 5, 6 are composed of a biocompatible flexible material that shields the contents of the prosthesis from body fluids so as to prevent interference of those body fluids with the functioning of prosthesis 1. Sleeves 5, 6 also prevent the contents of prosthesis 1 from damaging body tissue. Inner and outer sleeves 5, 6 may be made of any material conventionally used in other prostheses. Silicon or Teflon (polytetrafluoroethylene) materials may be considered.

Sleeve 4 encapsulates a linear assembly 50 of disklike cups or beads 7, an actuating mechanism 8 and a cable 11. The linear assembly 50 preferably includes a modified front segment 9 that has a recessed groove 30 for holding cable crimping ball 12 in a nested relation. Modified front segment 9 thus retains crimping ball 12 in a fixed position.

As shown, cable 11 passes through the center of cups or beads 7 and actuating mechanism 8. The distal end 10 of cable 11 is attached to modified front segment 9 and the proximal end 27 of cable 11 is attached to actuating mechanism 8 by the engagement between crimping ball 28 and cap 26.

As shown, each cup 7 (shown both in cross-section and in perspective) preferably has a generally circular outer wall 13 and a generally circular inner wall 14. In the embodiment shown in FIG. 1, inner wall 14 of each cup 7 borders an open upper surface 70 at the proximal end 72 of each cup 7. As shown in FIG. 1, this open upper surface 70 may be generally circular.

Each cup 7 also includes a substantially flat distal end 73 that includes a substantially flat inner surface 75 and a substantially flat outer surface 79. Generally circular outer wall 13, which defines the exterior wall of each cup 7, is attached at its lower end 78 to the substantially flat outer surface 79 and extends upward toward proximal end 72 of each cup 7. Generally circular outer wall 13 preferably has a radius that decreases from the radius at proximal end 72 of each cup 7 to the radius at substantially flat outer surface 79, As shown, a substantially bowl shaped cavity 71 is enclosed within each cup 7. Cavity 71 is bordered by open upper surface 70, inner wall 14 and substantially flat inner surface 75. Like outer wall 13, inner wall 14 preferably has a radius that decreases from the radius at proximal end 72 of each cup 7 to the radius at substantially flat inner surface 75.

As shown, a lower section 77 of the outer wall 13 of each cup 7 is enclosed within the inner wall 14 of the adjoining cup 7. Preferably, approximately one-half of outer wall 13 of each cup 7 is enclosed within the cavity 71, bordered by inner wall 14, when prosthesis 1 is in the erect state, as shown in FIG. 1. In the embodiment shown in FIG. 1, curved edges 17 of cups 7 maintain radial tension on sleeve 4, ensuring that the prosthesis will retain an appropriate diameter.

Cups 7 are preferably substantially short in length. In a preferred embodiment, the length of each cup 7, at its greatest length, is approximately equal to or less than one-half of the diameter of each cup 7, at its widest diameter. This relative cup length to cup diameter allows a large number of cups to be placed in the linear assembly 50 for a given length of prosthesis 1.

It also should be appreciated that in the embodiment shown in FIG. 1, the radius of outer wall 13 and the radius of inner wall 14 of each cup 7 both decrease semi-geometrically from the proximal end 72 of each cup 7 to substantially flat distal end 73 of each cup 7. In addition, the cavity 71, that inner wall 14 borders, preferably has a depth, at its greatest depth, that is approximately equal to one-half the greatest length of cup 7.

Figure 3:
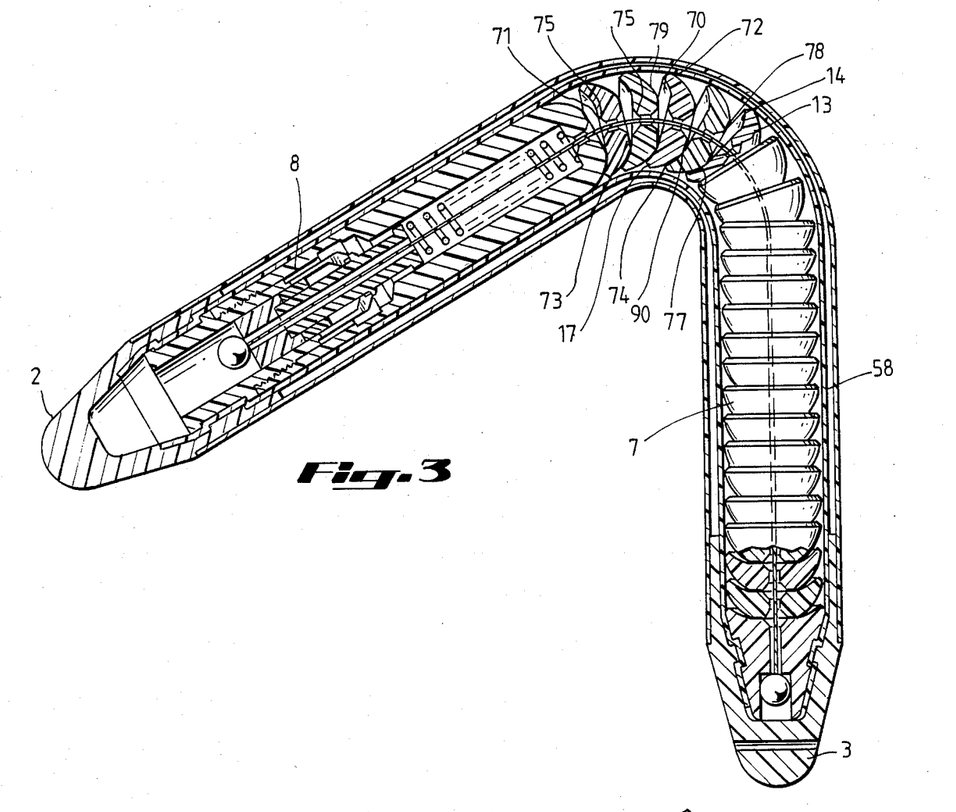
FIG. 3 is a cross-sectional view of an embodiment of the penile prosthesis of the present invention while in the flaccid state.

It should be appreciated that the substantially flat inner surface 75 allows outer wall 13 and substantially flat outer surface 79 of one cup 7 to slide along the inner surface 75 of an adjoining cup 7 as prosthesis 1 is being bent. Because substantially flat inner surface 75 does not obstruct this sliding movement of outer surfaces 13 and 79, prosthesis 1, as shown in FIG. 3, may be bent over a small radius. As prosthesis 1 is bent, outer wall 13 and outer surface 79 of one cup 7 maintain point contact with inner wall 14 and substantially flat inner surface 75 of an adjoining cup 7 as outer wall 13 and outer surface 79 slide along substantially flat inner surface 75. Because of this point contact between outer wall 13 and outer surface 79 of one cup 7 and inner wall 14 and inner surface 75 of an adjoining cup 7, prosthesis 1 maintains tension in cable 11 while being bent. This point contact, such as is shown at points 74, 90 in FIG. 3, thus enables prosthesis 1 to remain firm while being bent along a relatively small radius. This movement over a small radius allows the prosthesis to be rotated over a relatively large angular distance.

As shown in FIG. 1, outer wall 13 of each cup 7 does not contact inner wall 14 that borders cavity 71 of the adjoining cup 7. In this erect state, each cup 7 contacts its adjoining cup 7 only through the contact between the substantially flat outer surface 79 of cup 7 and the substantially flat inner surface 75 of an adjoining cup 7. This contact gives the prosthesis optimum axial or column strength, when the cups 7 are stacked-up to place the prosthesis in the erect position.

The lack of contact between outer wall 13 and inner wall 14 enables point contact during bending that permits the prosthesis to be bent along a relatively small radius. At the same time, this arrangement prevents dislodgement of cups 7 after cups 7 have been pulled together.

It is therefore apparent that the particular preferred design of cups 7 shown in FIG. 1 provides radial integrity and axial rigidity and, at the same time, allows large angular flexibility. This large angular flexibility allows increased positionability of prosthesis 1 and allows different operative approaches to be used for inserting the prosthesis.

As is further shown in FIG. 1, proximal segment 32 engages housing 18 of actuating mechanism 8. Housing 18 envelopes biasing member 19 and poppet 21, and engages fixed ring 20.

Figure 2:
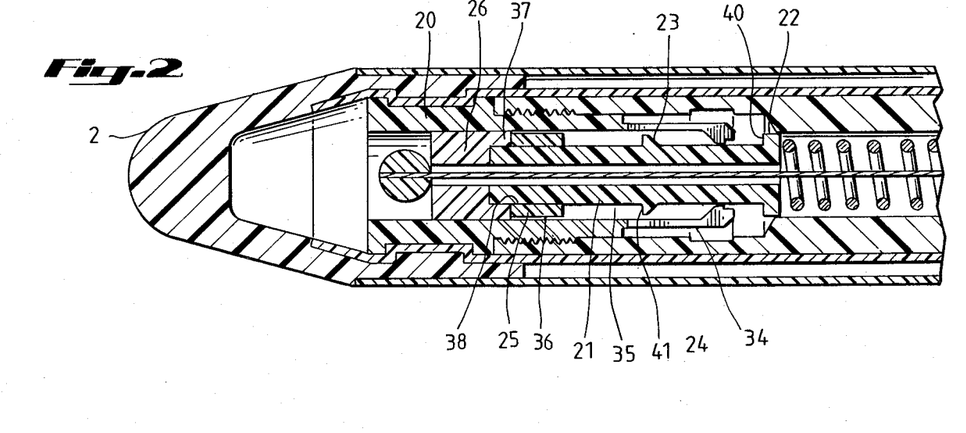
FIG. 2 is a cross-sectional view of the proximal end of an embodiment of the penile prosthesis of the present invention while in the erect state.

As is shown in FIG. 2, poppet 21 preferably includes a distal or first shoulder 22 and a proximal or second shoulder 23. Shown engaged to fixed ring 20 are flexible tines 24. Fixed ring 20 envelopes cap 26 and sliding ring 25. Cap 26 holds poppet 21 in a position that prevents proximal shoulder 23 from contacting proximal end 34 of tine 24. Sliding ring 25 slides along outer surface 35 of poppet 21. Outer surface 36 of sliding ring 25 may contact inner surface 37 of fixed ring 20 and inner surface 38 of sliding ring 25 contacts outer surface 35 of poppet 21.

In the embodiment shown in FIG. 1, biasing member 19 exerts a force against distal end 33 of housing 18 and distal end 39 of poppet 21. Accordingly, biasing member 19 forces poppet 21 in a direction away from distal end 33 of housing 18.

Flexible tines 24 are preferably movable from a position in which they may lock to the proximal sides 40, 41 of first shoulder 22 and second shoulder 23, respectively, to a position in which they cannot lock behind sides 40, 41. This flexibility of tines 24 enables sliding ring 25 to slide forward underneath tines 24 and to move tines 24 from a position in which they may lock behind side 41 to a position in which tines 24 may not lock behind side 41.

When ring 25 is in the position in which it has separated tines 24, biasing member 19, exerting a force upon distal end 39 of poppet 21, causes second shoulder 23 to engage ring 25, forcing both second shoulder 23 and ring 25 to the proximal side of tines 24. Once ring 25 and second shoulder 23 have been forced past tines 24, tines 24 snap back into a position in which they may engage side 40 of first shoulder 22. The stacking-up of cups 7 restrains further movement of poppet 21 toward proximal end 2 of prosthesis 1. Alternatively, contact between tines 24 and first shoulder 22 may restrain this further movement.

The inner parts of prosthesis 1 may be made of materials conventionally used in other mechanical penile prostheses. For example, biasing member 19, cable 11 and crimping balls 12 and 28 may be made of stainless steel. Housing 18, poppet 21, tines 24 and rings 20 and 25 may be made of either stainless steel or plastic.

A better appreciation of the manner in which the parts of prosthesis 1 interact, allowing manual movement of prosthesis 1 from a flaccid state to an erect state, should be gained from the following description of the manner of using the prosthesis of the present invention.

FIG. 1 shows the prosthesis 1 of the present invention in the erect state. In this position, tines 24 rest against outer surface 35 of poppet 21 on the proximal side of first shoulder 22. The force exerted by poppet 21 against crimping ball 28 pulls cups 7 into a tight configuration, taking any bends out of cable 11. Preferably, while in the erect state shown in FIG. 1, poppet 21 compresses biasing member 19 by about 20%. This compression results from cups 7 stacking up against one another to prevent further expansion of biasing member 19.

FIG. 3 shows the configuration of prosthesis 1 while in the flaccid state. Manual bending of prosthesis 1, either before or after being implanted in the penis, causes prosthesis 1 to alter its configuration from that shown in FIG. 1, when in the erect state, to that shown in FIG. 3, when it is in the flaccid state.

Figure 4:
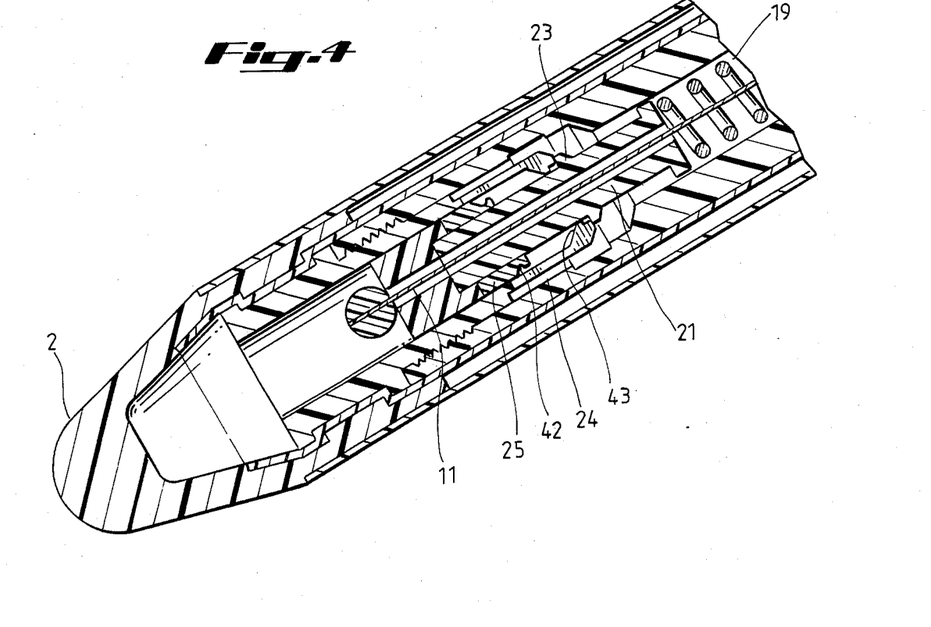
FIG. 4 is a cross-sectional view of the proximal end of an embodiment of the penile prosthesis of the present invention while in the flaccid state.

Movement from the erect state, shown in FIG. 1, to the flaccid state, shown in FIG. 3, is effected by a bending movement of prosthesis 1, causing crimping ball 28 to force poppet 21 toward distal end 3 of prosthesis 1 until second shoulder 23 passes to the distal side of tines 24. After shoulder 23 reaches this position, tines 24 snap behind shoulder 23, restraining movement of poppet 21 back toward proximal end 2 of prosthesis 1. While in this flaccid state, poppet 21 compresses biasing member 19 preferably by about 80%. FIG. 4 shows tines 24 locked behind second shoulder 23, corresponding to the position of actuating mechanism 8 when prosthesis 1 is in its flaccid state.

Cups 7 allow the bending of prosthesis 1 to effect the actuating force that cable 11, by way of crimping ball 28, exerts on poppet 21. As prosthesis 1 is bent, outer wall 13 and outer surface 79 of each cup 7 slides along substantially flat inner surface 75 of each adjoining cup 7, until shoulder 23 passes to the distal side of tines 24. The shape and arrangement of cups 7 allow prosthesis 1 to rotate about a relatively small radius, and simultaneously retain the radial integrity of sleeve 4. As shown in FIG. 3, the angular rotation of prosthesis 1 from its erectile state to its flaccid state may be as much as 120°.

To move prosthesis 1 from its flaccid state, shown in FIG. 3, to its erect state, shown in FIG. 1, cable 11 is moved toward distal end 3 until sliding ring 25 is pushed under tines 24. This further distal movement of cable 11 is effected by a bending movement that is in the same direction as was the bending movement that caused prosthesis 1 to be moved from its erect state to its flaccid state.

After prosthesis 1 has been bent far enough to pull ring 25 under tines 24, an erection is effected by releasing prosthesis 1, allowing prosthesis 1 to rotate to its erect position. This movement results because release of the bent prosthesis allows biasing member 19 to push poppet 21 through sliding ring 25, which remains in position underneath tines 24. Biasing member 19 pushes poppet 21 past sliding ring 25 until second shoulder 23 contacts sliding ring 25. Second shoulder 23 is forced against ring 25 and pushes ring 25 out from under tines 24, causing both second shoulder 23 and ring 25 to be forced to the proximal side of tines 24.

After biasing member 19 forces second shoulder 23 past tines 24, tines 24 snap into position on the proximal side of first shoulder 22. Further movement of poppet 21 is restrained when cups or beads 7 stack up, removing all slack in cable 11. Biasing member 19 remains in about 20% compression when cups 7 have been stacked up. This remaining compression keeps beads 7 under compression and keeps prosthesis 1, which is again in its erect position, firm.

FIG. 4 shows that sliding ring 25 may have a detent 42 for lodging prong 43 of tine 24. In this embodiment, detent 42 prevents sliding ring 25 from moving with poppet 21 toward the proximal end 2 of prosthesis 1 when biasing member 19 pushes poppet 21 in that direction, after ring 25 has moved tines 24 outwardly from the position in which tines 24 restrain movement of second shoulder 23.

Although FIG. 4 shows ring 25 with detent 42, this detent is not required to prevent ring 25 from moving with poppet 21 toward proximal end 2. The friction that tines 24 exert against ring 25 may hold ring 25 in place, allowing poppet 21 to pass through ring 25, even if ring 25 has a flat surface, as shown in FIGS. 1-3, that does not include detent 42.

Poppet 21 will slide through sliding ring 25 until second shoulder 23 strikes sliding ring 25. This striking action dislodges prong 43 from detent 42 (or dislodges ring 25 from the hold of tines 24 in an embodiment that does not include a ring 25 that has a detent 42), allowing second shoulder 23 to push sliding ring 25 toward the proximal end 2 of prosthesis 1 in response to the force that biasing member 19 exerts against poppet 21. Because sliding ring 25 does not move until struck by second shoulder 23, there is no space between sliding ring 25 and second shoulder 23 as poppet 21 slides toward proximal end 2 of prosthesis 1. Thus, tines 24 cannot lock between sliding ring 25 and second shoulder 23. Tines 24 therefore do not snap back into their restraining position until second shoulder 23 passes to the proximal side of tines 24. After second shoulder 23 has passed to the proximal side of tines 24, tines 24 snap back to their original position on the proximal side of first shoulder 22. After beads 7 are stacked up, all slack in cable 11 is removed and the movement of poppet 21 is restrained.

It should be appreciated that removal of first shoulder 22 from poppet 21 may still yield an operative device.

Figure 5A:
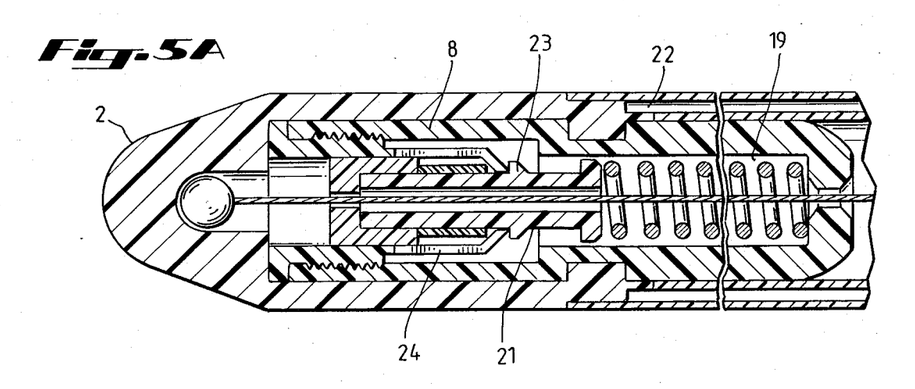
FIG. 5A is a cross-sectional view of the proximal end of an embodiment of the penile prosthesis of the present invention while in a super flaccid state.
Figure 5B:
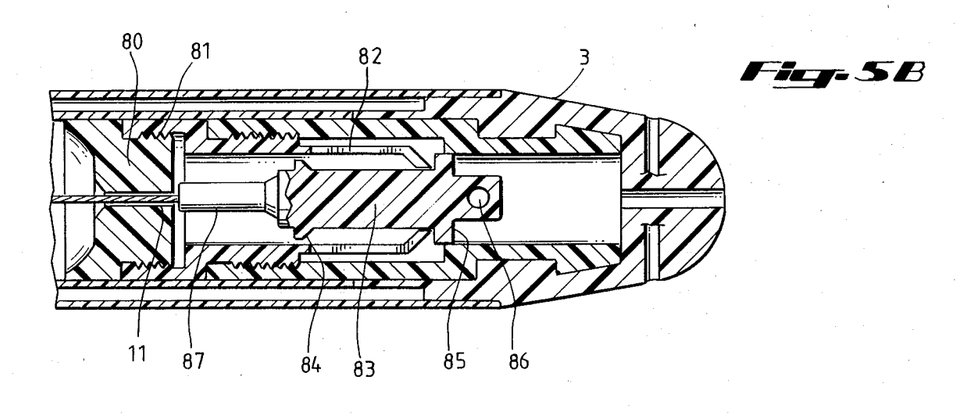
FIG. 5B is a cross-sectional view of the distal end of an embodiment of the penile prosthesis of the present invention that allows the prosthesis to be placed in a super flaccid state, showing the position of the prosthesis components while in the super flaccid state.
Figure 6:
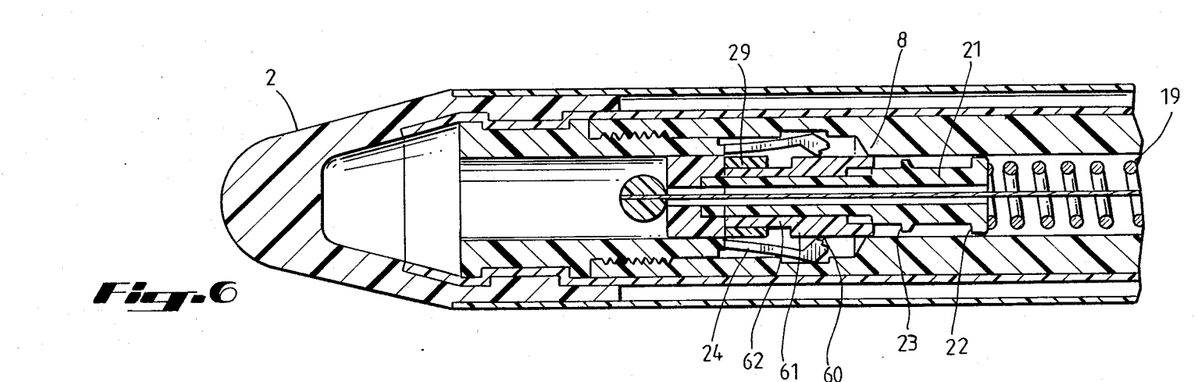
FIG. 6 is a cross-sectional view of the proximal end of a second embodiment of the penile prosthesis of the present invention that allows the prosthesis to be placed in a super flaccid state, showing the position of the prosthesis components prior to the prosthesis' movement to the erect state.
Figure 7:
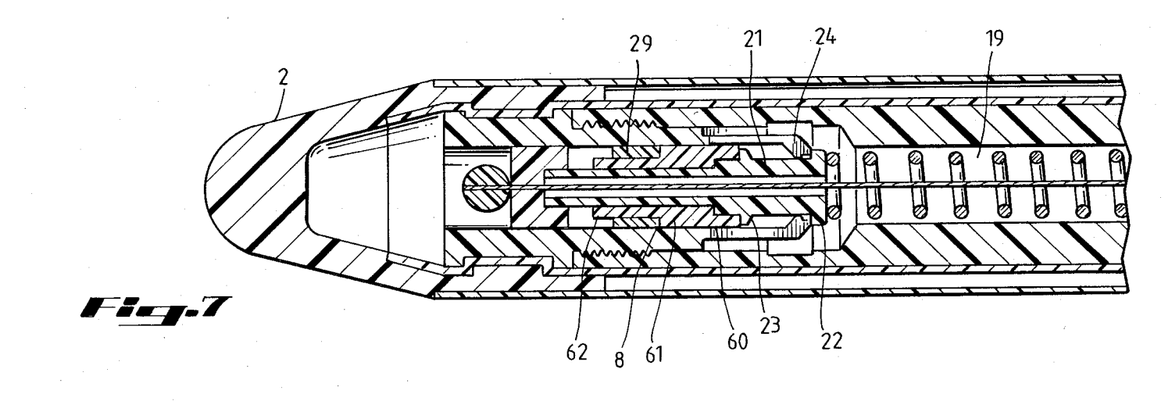
FIG. 7 is a cross-sectional view of the proximal end of a second embodiment of the penile prosthesis of the present invention that allows the prosthesis to be placed in a super flaccid state, showing the prosthesis in an erect state.

The penile prosthesis shown in FIGS. 1-4 is sufficiently flexible to permit implantation into the penis using all conventional surgical techniques. For implant purposes, however, the embodiments shown in FIGS. 5B, 6 and 7 provide prostheses that are even more flaccid. These embodiments enable an easier implantation through the scrotal or suprapubic surgical procedure than is permitted by the embodiment shown in FIGS. 1-4.

FIG. 5B shows distal end 3 of an embodiment of prosthesis 1 which may be placed in a super flaccid state. This embodiment includes distal cup or bead 80 engaged to ring 81. Distal cup 80 is aligned with the remaining beads 7 in linear assembly 50 (not shown). Ring 81 includes tines 82 that contact poppet 83. Poppet 83 includes proximal shoulder 84 and distal shoulder 85 along with orifice 86. Poppet 83 is connected to cable 11 at poppet 83's proximal end 87.

FIG. 5B shows this embodiment of prosthesis 1 while in its super flaccid state. When in this position, tines 82 rest against the proximal side of distal shoulder 85. To move prosthesis 1 from this super flaccid state to a flaccid state, a suture is first threaded through orifice 86. The suture is then pulled, which pulls poppet 83 toward distal end 3. After poppet 83 is pulled forward sufficiently to allow shoulder 84 to pass to the distal side of tines 82, tines 82 snap behind shoulder 84. Once tines 82 have snapped behind shoulder 84, prosthesis 1 attains its flaccid position and is ready for use.

FIG. 6 shows an alternative embodiment of prosthesis 1 which allows prosthesis 1 to be placed in a super flaccid state. In this embodiment, actuating mechanism 8 allows the prosthesis to be bent or stretched to a greater degree than the amount of stretch needed to cause the prosthesis shown in FIGS. 1-4 to move from a flaccid state to an erect state. The mechanism allowing this additional amount of stretch is the engagement of first sliding ring 60, having distal section 61 and proximal section 62, to second sliding ring 29, that envelopes proximal section 62 of first sliding ring 60. To move the prosthesis from its flaccid position to a super flaccid position, one manually bends the prosthesis until distal section 61 of first sliding ring 60 is pulled through tines 24. Tines 24 then snap into a restraining position on the proximal side of the distal section 61 of ring 60.

FIG. 6 shows this embodiment of prosthesis 1 in a position in which distal section 61 of sliding ring 60 has separated tines 24. This position may only be maintained so long as prosthesis 1 is held in the bent position that has forced cable 11 to pull distal section 61 into a position from which it causes tines 24 to separate.

Release of prosthesis 1 from this position would cause biasing member 19 to force second shoulder 23 into ring 60, causing ring 60 and second shoulder 23 to slide past tines 24. Once past tines 24, tines 24 would snap back to their original position, on the proximal side of first shoulder 22. The stacking up of cups 7 restrain movement of poppet 21 and enable prosthesis 1 to assume the erect position. The position of actuating mechanism 8 when the prosthesis is in the erect position is shown in FIG. 7.

Alternatively, if prosthesis 1 is further bent, from the position corresponding to that shown in FIG. 6, distal section 61 will be forced to the distal side of tines 24, tines 24 snapping behind distal section 61 onto proximal section 62. This position would correspond to the super flaccid position of prosthesis 1.

To deactivate the super flaccid state, prosthesis 1 is bent in the same direction, as it is bent to move prosthesis 1 from an erect to flaccid state and a flaccid state to a super flaccid state, until second sliding ring 29, sliding along proximal section 62 of ring 60, is pulled under tines 24. In this position, biasing member 19 is preferably compressed almost to solid height.

When prosthesis 1, which has been bent until second ring 29 slides under tines 24, is released, biasing member 19 pushes poppet 21 in the proximal direction until second shoulder 23 strikes first sliding ring 60. Poppet 21 and first sliding ring 60 then move together toward proximal end 2 until distal section 61 of first sliding ring 60 strikes second sliding ring 29. When distal section 61 of first sliding ring 60 strikes second sliding ring 29, second shoulder 23, distal section 61 of first sliding ring 60, and second sliding ring 29 are engaged so that there are no gaps between these three components.

Because of this arrangement, biasing member 19 continues to force poppet 21 toward proximal end 2 of prosthesis 1, allowing second ring 29, first sliding ring 60 and second shoulder 23 to pass underneath tines 24 until these three components pass to the proximal side of tines 24. FIG. 7, showing prosthesis 1 in the erect state, shows that second sliding ring 29, distal section 61 of first sliding ring 60, and second shoulder 23 remain engaged after they have slid past tines 24. Tines 24 then snap into a position on the distal side of second shoulder 23. The stacking up of cups 7 restrains further movement of biasing member 19.

Because of the distal end 3 in the embodiment shown in FIG. 5B and the arrangement of first sliding ring 60 and second sliding ring 29, in the embodiment of the penile prosthesis shown in FIG. 6, these embodiments of prosthesis 1 may attain two flaccid positions. One of these positions is for functional purposes, i.e., the position in which tines 82 lock to the proximal side of shoulder 84 in the FIG. 5B embodiment and the position in which tines 24 lock onto the proximal side of second shoulder 23 in the FIG. 6 and 7 embodiment. The other position is a surgical implantation position facilitating easier implantation of the prosthesis. This super flaccid position is the position in which tines 82 lie on the proximal side of shoulder 85 in the FIG. 5B embodiment and the position in which tines 24 lock behind the distal section 61 of first sliding ring 60 in the FIG. 6 and 7 embodiment.

In the FIG. 6 and 7 embodiment, it is apparent that additional rings could be added in the type of arrangement shown between first sliding ring 60 and second sliding ring 29 to enable the prosthesis to be adjusted to one or more positions in addition to those shown in the embodiment in FIG. 6. That is, second sliding ring 29 could be designed to have proximal and distal sections, and a third sliding ring could slide along the distal section of sliding ring 29.

It is apparent that a super flaccid state for implant purposes could be accomplished through other means. One such means could include a release mechanism, such as a button, in combination with one or two flat springs located on the distal side of first shoulder 22. In such an embodiment, the flat springs could snap onto the proximal side of first shoulder 22 when poppet 21 is advanced a distance comparable to the distance that poppet 21 is advanced when tines 24 snap behind first sliding ring 60 in the embodiment shown in FIG. 6. In this alternative embodiment, a button could be pressed to release the flat springs, causing them to retract from their restraining position and allowing biasing member 19 to force first shoulder 22 to the proximal side of the flat springs until the stacking up of cups 7 restrains any further distal movement.

Additional advantages and modifications will readily occur to those skilled in the art. For example, although the prosthesis described in the above embodiments is arranged such that the actuating mechanism 8 is located near the proximal end 2 of prosthesis 1 and the linear assembly 50 of cups 7 is located near the distal end 3 of prosthesis 1, the arrangement could be reversed such that actuating mechanism 8 is near the distal end 3 and the linear assembly 50 of cups 7 is near the proximal end 2. The invention in its broader aspects is therefore not limited to the specific details, representative apparatus, and the illustrative examples shown and described. Accordingly, departures may be made from the detail without departing from the spirit or scope of the disclosed general inventive concept.

I claim:

1. A penile prosthesis, having distal and proximal ends, for implantation in a penis, comprising:
   (a) an outer sleeve made of a biocompatible and flexible material;
   (b) a linear assembly of cups enclosed within said sleeve, each cup having an open proximal end and a substantially flat distal end, said substantially flat distal end having substantially flat inner and outer surfaces, said open proximal end accommodating the insertion of said substantially flat distal end of an adjoining cup such that said substantially flat outer surface of the substantially flat distal end of each cup is in substantially axial alignment with said substantially flat inner surface of each adjoining cup, when said prosthesis is in an erect state, each cup having a length that is shorter than its width, and wherein each said cup encloses a substantially bowl shaped cavity, said cavity bordered by an open upper surface at said proximal end of said cup, a generally circular inner wall, and said substantially flat inner surface at said substantially flat distal end of said cup, the radius of said generally circular inner wall decreasing from the radius at said proximal end of each said cup to the radius at said substantially flat inner surface, and wherein the substantially flat outer surface of the substantially flat distal end of each said cup engages the substantially flat inner surface of the substantially flat distal end of each adjoining cup, when said prosthesis is in an erect state, (c) a cable having distal and proximal ends and extending longitudinally within said prosthesis for maintaining said penile prosthesis in a state of tension; and (d) means for adjusting the position of said cable from a position in which the proximal end of said cable is nearer the proximal end of said prosthesis to a position in which said proximal end of said cable is moved closer to the distal end of said prosthesis, said means for adjusting the position of said cable allowing said movement of said cable to cause said prosthesis to move from an erect state to a flaccid state and allowing a further movement of said prosthesis in the same direction to return said prosthesis from said flaccid state to said erect state.

2. The penile prosthesis of claim 1, wherein the length of each cup, at its greatest length, is approximately equal to or less than one-half of the diameter of each cup, at its widest diameter.

3. A penile prosthesis, having distal and proximal ends, for implantation in a penis, comprising:

(a) an outer sleeve made of a biocompatible and flexible material;

(b) a linear assembly of cups enclosed within said sleeve, each cup having an open proximal end and a substantially flat distal end, said substantially flat distal end having substantially flat inner and outer surfaces, said open proximal end accommodating the insertion of said substantially flat distal end of an adjoining cup such that said substantially flat outer surface of the substantially flat distal end of each cup is in substantially axial alignment with said substantially flat inner surface of each adjoining cup, when said prosthesis is in an erect state, (c) a cable having distal and proximal ends and extending longitudinally within said prosthesis for maintaining said penile prosthesis in a state of tension; and (d) means for adjusting the position of said cable from a position in which the proximal end of said cable is nearer the proximal end of said prosthesis to a position in which said proximal end of said cable is moved closer to the distal end of said prosthesis, said means for adjusting the position of said cable allowing said movement of said cable to cause said prosthesis to move from an erect state to a flaccid state and allowing a further movement of said prosthesis in the same direction to return said prosthesis from said flaccid state to said erect state, said means for adjusting the position of said cable including a poppet, longitudinally arranged at the distal side of said proximal end of said cable, and in which said prosthesis further includes a biasing member for exerting a force against said poppet to maintain said poppet in a fixed position, said poppet including a shoulder, and a restraining means for restraining movement of said shoulder, said prosthesis being in its flaccid state when said shoulder engages said restraining means.

4. The penile prosthesis of claim 3, wherein said restraining means includes a flexible tine, said tine moveable from a position in which it may contact said shoulder and restrain movement of said shoulder to a position in which it may not contact said shoulder and may not restrain movement of said shoulder.

5. The penile prosthesis of claim 4, wherein said tine is engaged to a fixed ring located within said sleeve, said fixed ring encircling said poppet, and in which said prosthesis further includes a first sliding ring, the inner surface of said first sliding ring engaging the outer surface of said poppet, said first sliding ring aligned with said shoulder and said tine such that movement of said cable toward said distal end of said prosthesis causes said first sliding ring to move said tine to a position in which it cannot engage said shoulder, said movement of said tine allowing said biasing member to force said shoulder into contact with said first sliding ring enabling said shoulder to be forced to said proximal side of said tine, said tine snapping back to its engagement position, after said shoulder has been forced past said tine.

6. The penile prosthesis of claim 5 further comprising a means for placing said prosthesis in a super flaccid state.

7. The penile prosthesis of claim 6 wherein said means for placing said prosthesis in said super flaccid state includes:

a second poppet engaged to the distal end of said cable, said second poppet including first and second shoulders; and a tine movable from a position in which it may restrain movement of said first shoulder to a position in which it may restrain movement of said second shoulder;

said prosthesis being in its super flaccid state when said tine engages said first shoulder and being in its flaccid state when said tine engages said second shoulder.

8. The penile prosthesis of claim 6 wherein said means for placing said prosthesis in said super flaccid state includes a second sliding ring and wherein said first sliding ring includes a proximal section and a distal section, said second sliding ring enabling said penile prosthesis to be placed in a super flaccid state by allowing said distal section of said first sliding ring to be pulled to the distal side of said tine, allowing said tine to lock to said proximal section of said first sliding ring, an additional movement of said cable towards the distal end of said prosthesis allowing said second sliding ring to separate said tine from its engaged position, enabling said biasing member to force said distal section of said first sliding ring and said shoulder from the distal side of said tine to the proximal side of said tine.

9. A penile prosthesis for implantation in a penis, comprising:
  (a) an outer sleeve made of a biocompatible and flexible material;
  (b) a linear assembly of cups enclosed within said sleeve, each cup having an open proximal end and a substantially flat distal end, said distal end having substantially flat inner and outer surfaces, said open proximal end accommodating the insertion of said distal end of an adjoining cup such that said substantially flat outer surface of the distal end of each cup is in substantially axial alignment with said substantially flat inner surface of each adjoining cup, when said prosthesis is in an erect state;
  (c) a cable having distal and proximal ends and extending longitudinally within said prosthesis for maintaining said penile prosthesis in a state of tension;
  (d) a poppet, longitudinally arranged at the distal side of said proximal end of said cable, said poppet having first and second shoulders longitudinally arranged on said poppet;
  (e) a biasing member for exerting a force against said poppet to maintain said poppet in a fixed position;
  (f) a fixed ring located within said sleeve, said fixed ring encircling said poppet;
  (g) a flexible tine, engaged to said fixed ring, for restraining movement of said first and second shoulders when in a position in which said tine may contact said shoulders, and movable to a position in which said tine may not contact said shoulders;
  (h) a sliding ring, the inner surface of said sliding ring engaging the outer surface of said poppet, said sliding ring aligned with said shoulders and said tine such that movement of said cable toward said distal end of said prosthesis may cause said sliding ring to move said tine to a position in which it cannot engage said shoulders.

10. A penile prosthesis for implantation in a penis, comprising:
  (a) an outer sleeve made of a biocompatible and flexible material;
  (b) a linear assembly of cups enclosed within said sleeve, each cup having an open proximal end and a substantially flat distal end, said distal end having substantially flat inner and outer surfaces, said open proximel end accommodating the insertion of said distal end of an adjoining cup such that said substantially flat outer surface of the distal end of each cup is in substantially axial alignment with said substantially flat inner surface of each adjoining cup, when said prosthesis is in an erect state;
  (c) a cable having distal and proximal ends for extending longitudinally within said prosthesis for maintaining said penile prosthesis in a state of tension;
  (d) a poppet, longitudinally arranged at the distal side of said proximal end of said cable, said poppet having first and second shoulders longitudinally arranged on said poppet;
  (e) a biasing member for exerting a force against said poppet to maintain said poppet in a fixed position;
  (f) a fixed ring located within said sleeve, said fixed ring encircling said poppet;
  (g) a flexible tine, engaged to said fixed ring, for restraining movement of said first and second shoulders when in a position in which said tine may contact said shoulders, and movable to a position in which said tine may not contact said shoulders;
  (h) a first sliding ring, the inner surface of said first sliding ring engaging the outer surface of said poppet, said first sliding ring having proximal and distal sections and being aligned with said shoulders and said tine such that movement of said cable toward said distal end of said prosthesis may cause said first sliding ring to move said tine to a position in which it cannot engage said shoulders;
  (i) a second sliding ring, the inner surface of said second sliding ring in contact with the outer surface of said proximal section of said first sliding ring, said second sliding ring aligned with said shoulders, said tine, and said first sliding ring such that movement of said cable toward said distal end of said prosthesis may cause said second sliding ring to move said tine to a position in which it cannot engage said shoulders or said distal section of said first sliding ring.

11. A penile prosthesis, having distal and proximal ends, for implantation in a penis, comprising:
  (a) an outer sleeve made of a biocompatible and flexible material;
  (b) a linear assembly of cups enclosed within said sleeve, each cup having an open proximal end and a substantially flat distal end, said distal end having substantially flat inner and outer surfaces, said open proximal end accommodating the insertion of said distal end of an adjoining cup such that said substantially flat outer surface of the distal end of each cup is in substantially axial alignment with said substantially flat inner surface of each adjoining cup, when said prosthesis is in an erect state;
  (c) a cable having distal and proximal ends and extending longitudinally within said prosthesis for maintaining said penile prosthesis in a state of tension;
  (d) means for adjusting the position of said cable from a position in which the proximal end of said cable is nearer the proximal end of said prosthesis to a position in which said proximal end of said cable is moved closer to the distal end of said prosthesis, said means for adjusting the position of said cable allowing said movement of said cable to cause said prosthesis to move from an erect state to a flaccid state and allowing a further movement of said prosthesis in the same direction to return said prosthesis from said flaccid state to said erect state; and
  (e) means for placing said prosthesis in a super flaccid state.

12. The penile prosthesis of claim 11 wherein said means for placing said prosthesis in said super flaccid state includes:
  a poppet engaged to the distal end of said cable, said poppet including first and second shoulders; and
  a tine movable from a position in which it may restrain movement of said first shoulder to a position in which it may restrain movement of said second shoulder;
  said prosthesis being in its super flaccid state when said tine engages said first shoulder and being in its flaccid state when said tine engages said second shoulder.

* * * * *